US008895321B2

(12) United States Patent
Lopez et al.

(10) Patent No.: US 8,895,321 B2
(45) Date of Patent: Nov. 25, 2014

(54) INTEGRATED AFFINITY MICROCOLUMNS AND AFFINITY CAPILLARY ELECTROPHORESIS

(75) Inventors: Gabriel Lopez, Albuquerque, NM (US); Linnea Ista, Albuquerque, NM (US); Steven RJ Brueck, Albuquerque, NM (US); Aurelio Evangelista Lara, Albuquerque, NM (US); Mangesh Bore, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 869 days.

(21) Appl. No.: 13/104,200

(22) Filed: May 10, 2011

(65) Prior Publication Data

US 2014/0110258 A1    Apr. 24, 2014

Related U.S. Application Data

(62) Division of application No. 12/102,663, filed on Apr. 14, 2008, now Pat. No. 7,959,861.

(60) Provisional application No. 60/973,712, filed on Sep. 19, 2007.

(51) Int. Cl.
*G01N 33/537* (2006.01)
*G01N 27/447* (2006.01)

(52) U.S. Cl.
CPC .................. *G01N 27/44721* (2013.01)
USPC ........ 436/538; 436/518; 436/536; 435/283.1; 435/287.1; 435/287.2; 435/288.7

(58) Field of Classification Search
USPC ............ 436/518, 536, 538; 435/283.1, 287.1, 435/287.2, 288.7
See application file for complete search history.

(56) References Cited

U.S. PATENT DOCUMENTS

| 5,783,397 | A | * | 7/1998 | Hughes et al. ................. 435/7.1 |
| 5,958,202 | A | * | 9/1999 | Regnier et al. ................. 204/451 |
| 6,074,827 | A | * | 6/2000 | Nelson et al. ................. 435/6.12 |
| 2006/0169587 | A1 | * | 8/2006 | Lopez et al. ................. 204/451 |

* cited by examiner

*Primary Examiner* — Melanie Y Brown
(74) *Attorney, Agent, or Firm* — Gonzales Patent Services; Ellen M. Gonzales

(57) ABSTRACT

Device and method for detecting the presence of known or unknown toxic agents in a fluid sample. Targets in the sample are bound to releasable receptors immobilized in a reaction region of a micro- or nano-fluidic device. The receptors are selected based on their affinity for classes of known toxic agents. The receptors are freed and the bound and unbound receptors separated based on differential electrokinetic mobilities while they travel to a detection device.

5 Claims, 7 Drawing Sheets

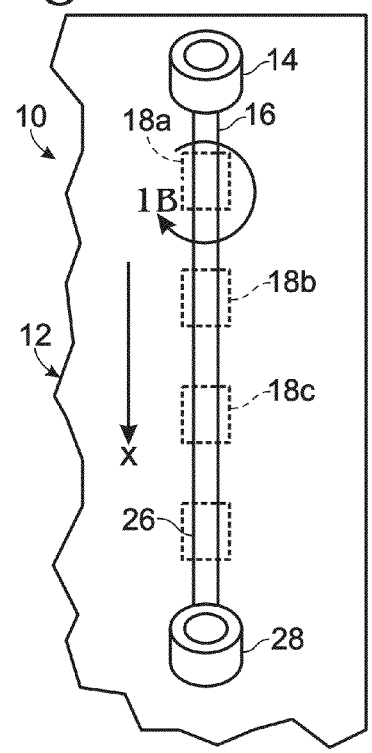
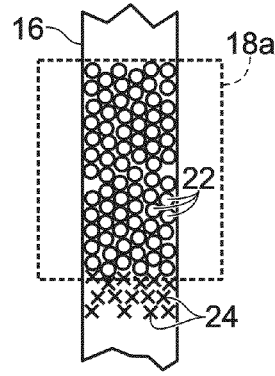
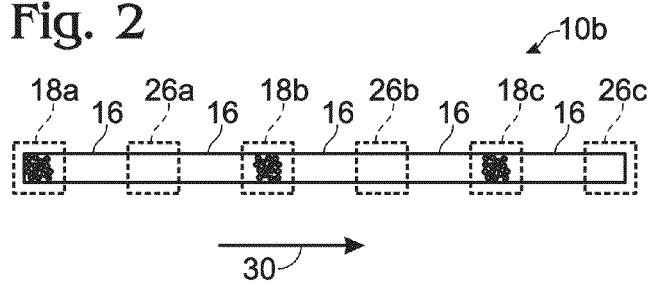
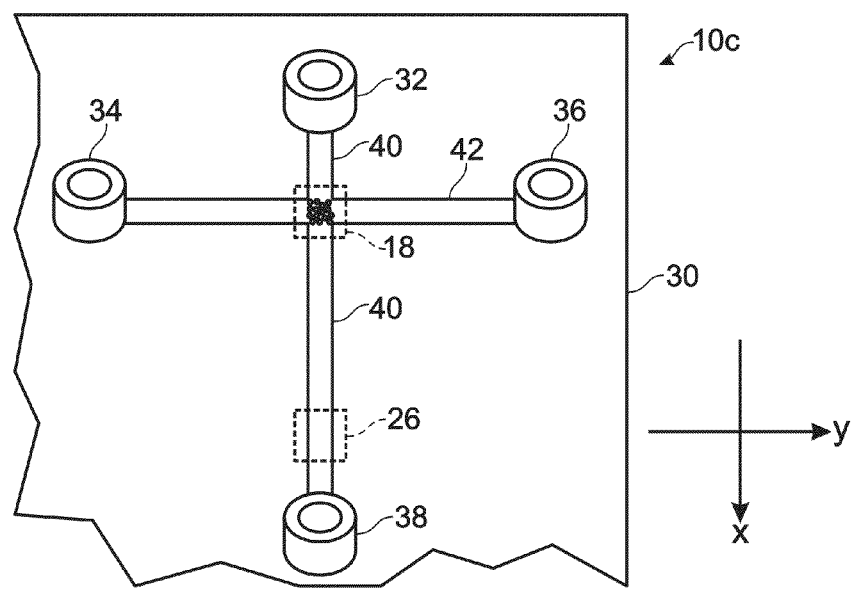

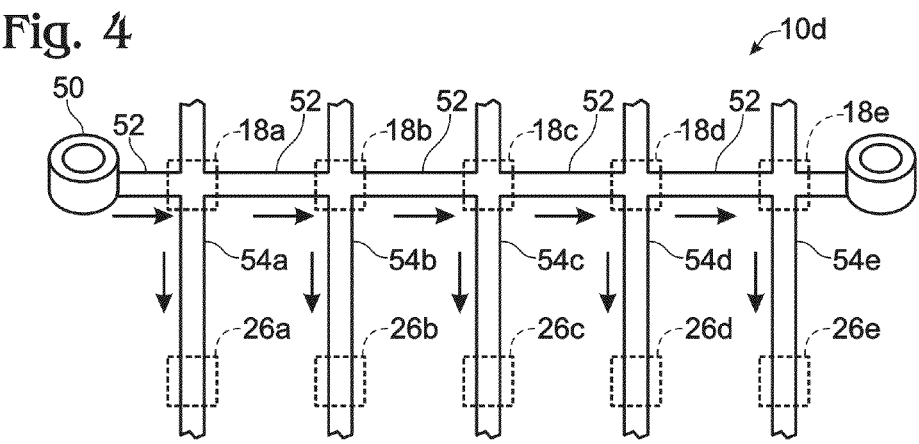
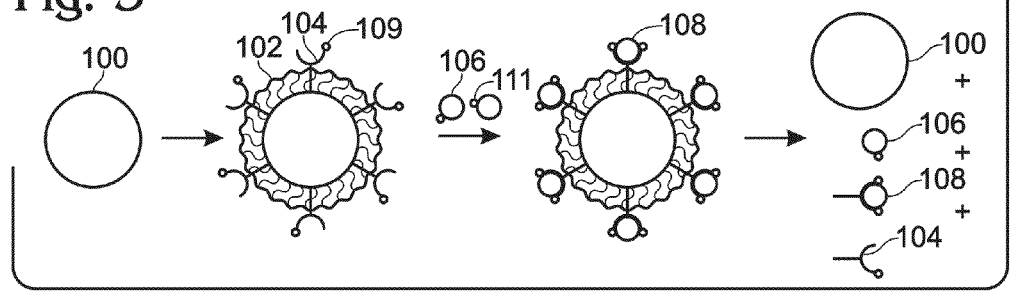
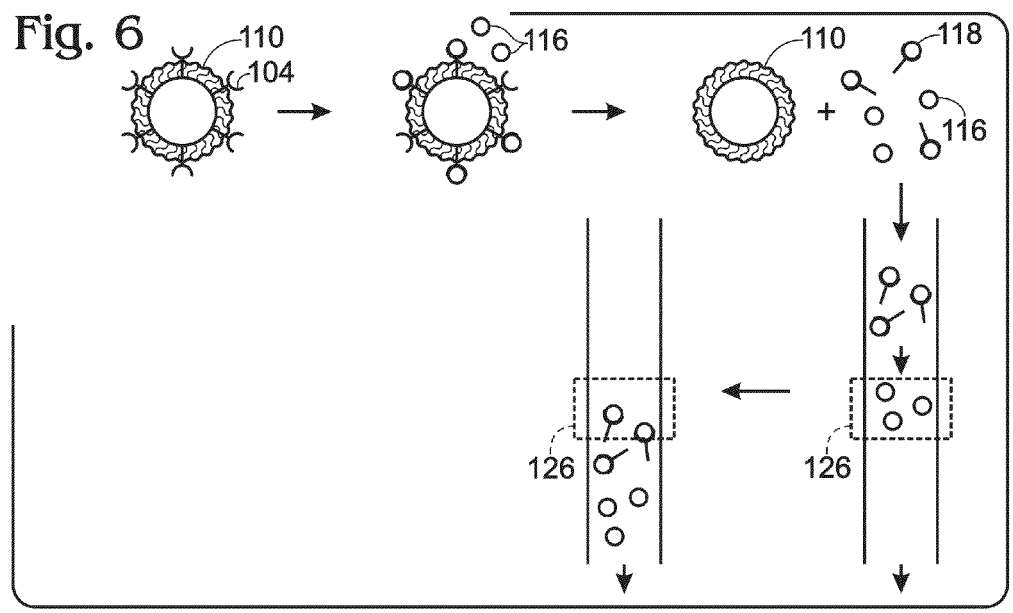

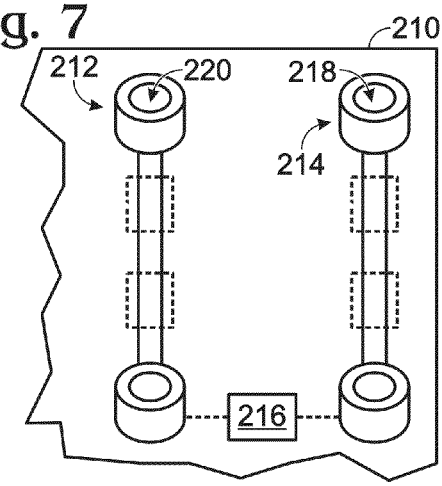
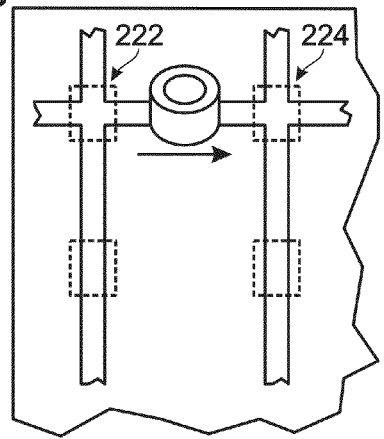
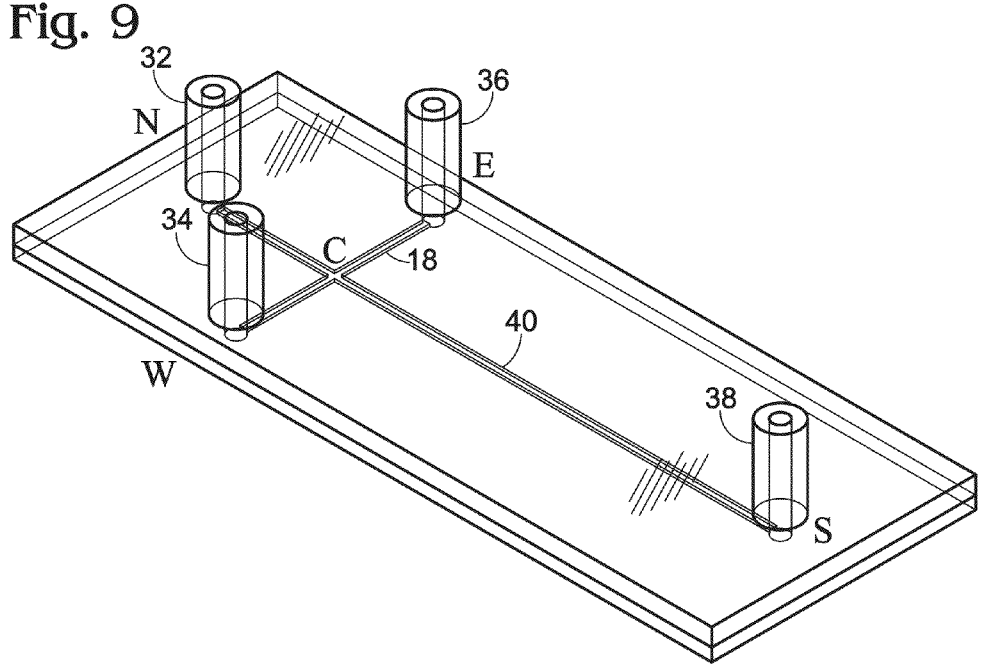

Fig. 10
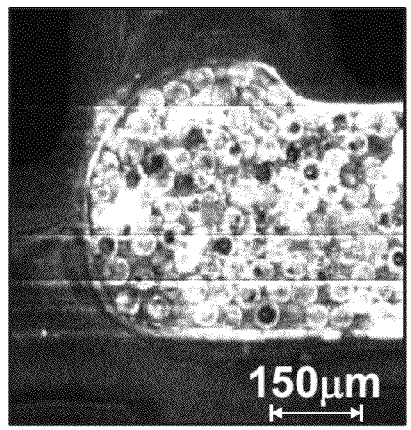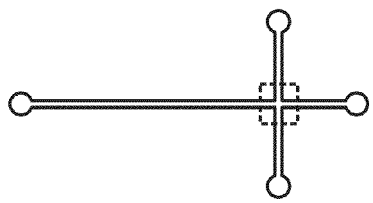
Fig. 11
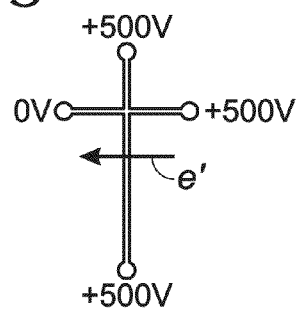
Fig. 12
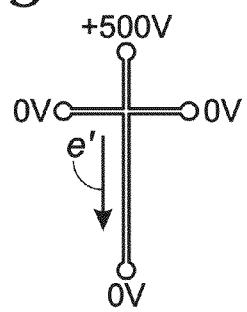
Fig. 13
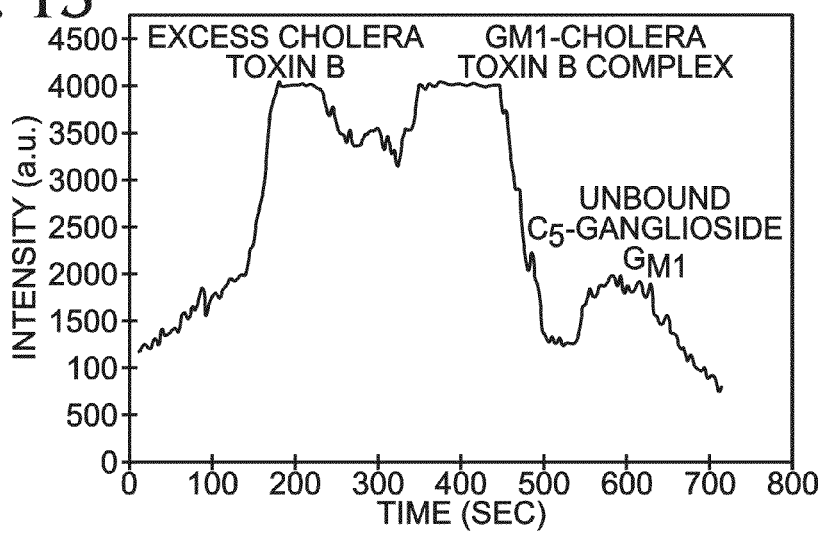

Fig. 14

[Graph: Intensity (a.u.) vs. Concentration of Cholera Toxin Subunit B (micro milar)]

INTEGRATED AFFINITY MICROCOLUMNS AND AFFINITY CAPILLARY ELECTROPHORESIS

PRIORITY CLAIM

The present application is a divisional application of U.S. patent application Ser. No. 12/102,663, filed Apr. 14, 2008, now U.S. Pat. No. 7,959,861, which claims priority to U.S. Provisional Patent Application No. 60/973,712, filed Sep. 19, 2007, both of which are hereby incorporated by reference.

FEDERALLY SPONSORED RESEARCH

This invention was made with government support under Grant No. 0515684 awarded by the National Science Foundation. The government has certain rights in this invention.

BACKGROUND AND SUMMARY

It is widely acknowledged that there has been an increased threat of chemical and biological weapons (CBWs). Recent events have made it clear that CBWs pose a potential threat not only on the battlefield, but also as agents of terrorism. The agents under consideration range from low molecular weight compounds such as organophosphorus nerve agents to invasive cells and viruses. In addition, many of these agents are already established public health problems. See, e.g. Paddle B M. 2003. Therapy and prophylaxis of inhaled biological toxins. *Journal of Applied Toxicology* 23: 139-70, which is incorporated herein by reference.

Accordingly, detection of CBW agents is a continuing and accelerating intelligence challenge. Detection of CBW agents is an exceptionally demanding problem because the amounts of CBW agent sufficient to cause harm to humans is typically very small, requiring exceptional sensitivity. Moreover, rapid identification and remediation is frequently necessary. Even more worrisome, with advances in biological synthesis capabilities, creation of new CBW agents is no longer exclusively a nation-state enterprise with large-scales observables, but is becoming a garage enterprise—on the scale of methamphetamine labs—with widespread availability to potential adversaries.

Most current threat detection systems utilize immunology, PCR, or spectroscopic detection-based technologies which rely on precise identification of the biological or chemical toxin involved. While this approach has its uses, it is ineffective against either newly developed or modified threats that, by novelty or design, can evade precise recognition elements.

Accordingly, there is a need for widely dispersible, inexpensive sensors that are able to monitor large areas for a wide variety of both known and unknown agents. Accordingly, a chip-scale technology that is sensitive to a variety of agent classes and that requires only very small sample volumes is needed.

Accordingly, in one embodiment, the present disclosure provides a microscale, multi-threat agent detection system that is able to detect both known and unknown agents by detection of physiological responses associated with exposure to a toxic agent, rather than the presence of specific toxins. In this strategy, the potential physiological effect is key, and the exact identify of the threat agent is secondary. Detection of physiological responses allows for rapid intervention and/or prophylaxis to block mortality and morbidity among potential target populations. Because the detector exploits the target of the threat, or one of the targets of the threat, either novel threats, or those deliberately designed to thwart current detections schemes, are quickly detected.

Moreover, at least in some embodiments, the system described herein, allows at least low level quantification of the ability of the threat to bind to the target physiological molecule, thus allowing for proper (or at least improved estimates of the proper) dosage of counter acting agents.

It will be appreciated that the need for such systems is apparent for a variety of applications, not limited to simply detection of CBW agents, but also including intelligence gathering, battlefield readiness, general public health, and both clinical and basic research. Accordingly, in at least some embodiments, the system described herein is envisioned as an important component for future medical diagnostic and drug discovery applications, as well as being a possible means of rapid and efficient proteomic analysis.

BRIEF DESCRIPTION OF THE DRAWINGS

FIG. 1A is a schematic illustration of an exemplary detector according to a first embodiment.

FIG. 1B is a close up view of section of FIG. 1A.

FIG. 2 is a schematic illustration of an exemplary detector according to a second embodiment.

FIG. 3 is a schematic illustration of an exemplary detector according to a third embodiment.

FIG. 4 is a schematic illustration of an exemplary detector according to a fourth embodiment.

FIG. 5 is a schematic illustration of a method according to an embodiment employing the use of receptors encased in a lipid bilayer formed around a bead.

FIG. 6 is a schematic illustration of a method employing receptors reversibly absorbed in a smart surface.

FIG. 7 is a schematic illustration of an exemplary detector according to a fifth embodiment.

FIG. 8 is a schematic illustration of an exemplary detector according to a sixth embodiment.

FIG. 9 shows a PDFMS microchannel with packed glass beads according to the first Example.

FIG. 10 shows a confocal microscopy image of 30 μm glass beads with $C_5$-ganglioside $G_{M1}$ receptor labeled with BODIPY dye packed in the PDMS microchannel of FIG. 8.

FIG. 11 shows voltages applied to different wells during sample injection.

FIG. 12 shows voltages applied to different wells during release and separation.

FIG. 13 shows separation of receptor and receptor-ligand complex (4 μM Cholera Toxin Subunit B).

FIG. 14 shows the binding curve for Cholera Toxin Subunit B and $C_5$-ganglioside $G_{M1}$ receptor.

FIG. 15 provides fluorescence images of GM1 bearing beads packed in the microchannel. Red signal is from cholera toxin B conjugated with the fluorophore, Alexa 555 and green signal is from GM1 receptor conjugated with the fluorophore, Bodipy FL. (a) Before injection of cholera toxin B sample; (b) after injection of 100 nM cholera toxin B and washing; (c) after electrokinetic elution of GM1 and cholera toxin B with 10 wt % sodium dodecyl sulfate.

DETAILED DESCRIPTION

Figure 16:
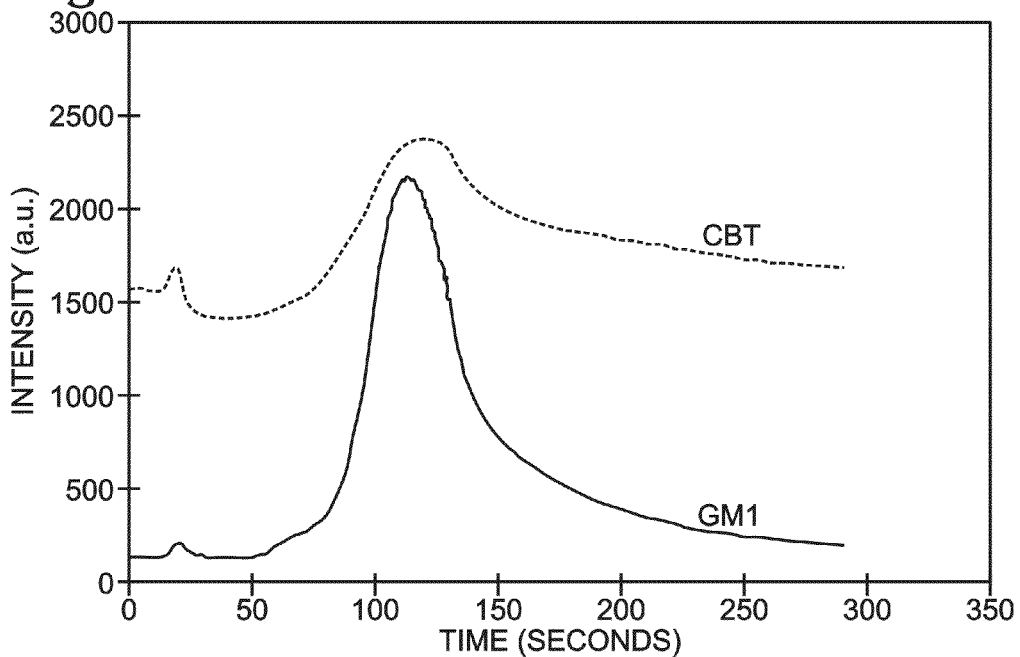
FIG. 16 shows the electrokinetic elution of GM1-cholera toxin B using 10 wt % sodium dodecyl sulfate. The green line (below) represents the elution of GM1, while the red line represents the elution of cholera toxin B.

Various embodiments of the present disclosure are configured to identify the presence of a target using toxin receptor binding and electrokinetic separation. In general, the present disclosure provides a detection system wherein a fluid sample is injected into the detector and allowed to interact with receptors reversibly immobilized in a reaction region. The receptors comprise known receptors that have been identified as being receptors for known targets or classes of targets (e.g. threat agents). It will be appreciated that according to various embodiments, the receptors may take the form of naturally-occurring or synthesized versions of known receptors, naturally-occurring or synthesized versions of modified known receptors, and/or naturally-occurring or synthesized versions of biomimetics of known receptors. The receptors may be fluorescently or otherwise labeled. Alternatively, because the presently disclosed methods rely on different mobilities for the receptor-ligand complex and the receptor, methods that utilize detection methods that do not require a label could be employed. Examples of suitable detection systems that do not necessarily require a label include, but are not limited to electrical, acoustical, or UV detectors. If present, the target binds the receptors in the reaction region. Conditions are then altered such that the immobilized receptors are released from the reaction region, allowing both bound and unbound receptors to travel through a micro- or nano-fluidic channel in the detector to a detection region. As the receptors traverse the micro- or nano-fluidic channel, the bound and unbound receptors are separated in time based on the different electrokinetic mobilities of the bound and unbound receptors. The passage of the receptors through the detection region is then monitored (e.g. by detecting the presence of a fluorescent label on the receptors) and based on when signal is detected, a determination can be made as to whether the sample passing through the detection region included only unbound receptors (and therefore no target) or bound receptors (therefore determining that the sample tested positive for presence of the target).

Turning to FIG. 1A, a schematic illustration of an exemplary detector 10 according to a first embodiment is shown. A silicon chip 12 includes two fluid injection columns 14 and 28 connecting a microfluidic channel 16. Columns 14 and 28 are in fluidic communication with microfluidic channel 16 so as to allow for the introduction the various buffers, regents, and sample(s) into microfluidic channel 16. Microfluidic channel 16 includes one or more reaction regions 18, (shown in FIG. 1 as reaction regions 18a, 18b and 18c) and a detection region 26. A close up of a reaction region 18a is shown in FIG. 1B.

Each reaction region includes a target concentrating mechanism comprising releasably immobilized receptors known to bind one or more classes of target agents. In the depicted embodiment, the target concentrating mechanism comprises biologically active beads 22. For purposes of the present description, the term "biologically active beads" is intended to describe beads that are capable of interacting with one or more target biological agents that may or may not be present in a sample solution introduced into the detection device. For example, the surface of the beads may present one or more target-specific receptors. More specific examples of biologically active beads will be described below. In general, the receptors are associated with the target concentrating mechanism in such a way that they are immobilized by the target concentrating mechanism under a first set of conditions and are released by the target concentrating mechanism under a second set of conditions. For the purposes of the present disclosure when a receptor is referred to as being "immobilized" by the target concentrating mechanism in the reaction region it is meant that the receptor is prevented from leaving the confines of the reaction region. Several non-limiting mechanisms for immobilization are described in greater detail below. Accordingly, when a receptor is "released" by the target concentrating mechanism, it is meant that the receptor, and any target to which the receptor is bound, is able to travel away from the reaction region.

Microfluidic channel 16 is further in communication with a fluid manipulation source, which is capable of controlling fluid flow in one or more desired directions. Accordingly, a sample fluid is introduced in column 14 and encouraged to flow in the x direction, shown by the arrow towards the reaction and detection regions 18 and 26. Suitable fluid manipulation sources include external hydraulic pumps, electrodes configured to induce electro-osmotic pumping, pressure-driven flow, combinations thereof, and the like.

Depending on the desired detection profile of the detector, reaction regions 18a, 18b, and 18c may include the same or different receptors configured to bind the same or different targets. For example, a first reaction region could include receptors known to bind a first class of threat agents or associated with a first physiological effect, while a second reaction region could include receptors known to bind a second class of threat agents or associated with a second physiological threat. Of course it will be understood that while three reaction regions are shown for illustrative purposes, more or fewer reaction regions could be utilized depending on the desired detection profile.

FIG. 2 depicts another embodiment of a detector 10b according to the present disclosure. In this embodiment, the microfluidic channel includes a plurality of detection regions, 26a, 26b, and 26c. As with the embodiment shown in FIG. 1, reaction regions 18a, 18b, and 18c may include the same or different receptors configured to bind the same or different targets. Furthermore, the mechanism(s) used for detection in detection regions 26a, 26b, and 26c may be the same or different in each region. Again it will be understood that the number of detection and reaction regions shown is for illustrative purposes only and should not be considered in a limiting fashion.

FIG. 3 depicts yet another embodiment of a detector 10c according the present disclosure. In this embodiment, the chip 30 includes two microfluidic channels 40 and 42 in a t-pattern. The terminal end of each channel is in fluidic communication with a column: identified as columns 32, 34, 36, and 38, respectively. The long end of the "t" shape includes one or more reaction regions 18 and one or more detection regions 26. It will be appreciated that the configurations of either FIG. 1 or FIG. 2 may be employed or that alternative, suitable configurations for the reaction and detection regions may be employed. In this embodiment, fluid manipulation source are used to control fluidic movement in the x and y directions. In practicality, if this geometry is used, it may be necessary to employ three fluid manipulation sources, one to encourage movement in the y direction during the reaction phase, one to encourage movement in the x direction during the reaction phase, and one to discourage movement in the y direction during the detection phase. In this embodiment, a fluid sample is introduced into channel 34 and then moved along channel 42 (e.g. in the y direction) towards the reaction chamber 18 at the intersection with channel 40. Reversibly immobilized receptors inside of reaction chamber 18 bind the target, while waste is allowed to continue down channel 42 (continuing in the y-direction) towards column 36. The immobilized receptors are then released from by the target concentration mechanism (as described in greater detail below) and encouraged to flow down microcolumn (or "detection lane") 40 (in the x direction) towards detection region 26.

Turning now to FIG. 4, it can be seen that the geometry shown in FIG. 3 can be expanded to provide multiple detection lanes, thereby providing a two-dimensional arrayed detector 10$d$. In this example, a sample is introduced to column 50 and encouraged to flow through microchannel 52 through a series of reaction regions 18$a$-18$e$. Each reaction region may, for example, include receptors selected to interact with the same or a different target or a different class or type of target. Conditions are selected such that any target present within the sample is able to bind suitable receptors with the desired degree of specificity. Then, conditions are altered, as described in greater detail below, such that the target concentrating mechanism releases the receptors. The bound and unbound receptors are then encouraged to flow down an associated microchannel 54$a$-54$e$, (i.e. microchannel 54$a$ for reaction region 18$a$) towards the corresponding detection region 26$a$-26$e$ (i.e. detection region 26$a$ for reaction region 18$a$). Conditions are provided such that during the travel from the reaction region to the detection region, the bound and unbound receptors separate from each other and the timing of the passage of the receptors through the detection region is monitored.

It should be appreciated that any geometry may be employed in the presently-described detection system. For example, in some cases the geometry may, at least in part, be determined by the different mobilities of the receptor and receptor-ligand complex. As the mobilities of the receptor and receptor-ligand complex are more similar, a longer separation pathway may be required in order to attain detectable separation. Accordingly, non-linear geometries including U-shapes, spirals, or the like may be employed in order to attain the desired separation while confining the system to a given space. Furthermore, in some cases it may be possible or even desirable to use 3-dimensional geometries. Moreover, it will be appreciated that the mechanism(s) used to encourage fluid flow in the system may be affected and/or determined by the particular geometry used. Accordingly, 3-dimensional (or some 2-dimensional) geometries may employ gravity-driven, magnetically-driven or cryogenically-driven fluid flow systems in additional to or as an alternative to the various fluid-flow mechanisms identified above.

It will be appreciated that the microchannels described herein may be formed using any suitable method including by employing standard photolithography techniques. An example of a useful technique for fabricating the chips herein is described in O'Brien et al. 2003 "Fabrication of an integrated nanochip using interferometric lithography." *Journal of Vacuum Science and Technology B* 21: 2941-5, which is hereby incorporated by reference. Generally, interferometric lithography (IL) and lift off are used to form a nanopatterned hard metal (e.g., mask) over the entire surface of a silicon wafer (e.g., 2"). Conventional projection lithography techniques are then used to delineate with photoresist the areas corresponding to the microfluidic (e.g., 200 µm wide) connections, the microscale grating structures within the microfluidic channels (which may be used to trap the beads in the reaction region(s) and shown, for example, in FIG. 1B at 24), the macroscale (2 mm dia.) reservoirs at the ends of the microfluidic streams, and the entire nanochannel array (analysis stream). The patterned (IL hard mask and conventional photoresist) chip is then subjected to reactive ion etching to form the three dimensional relief of the analytical chip. Upon removal of the photoresist and the hard mask, cleaning, and oxidation as desired, the entire fluidic system is enclosed by anodic bonding of a transparent solid (such as Pyrex® glassware available from World Kitchen, LLC) "roof" (that contains the interface ports) over the entire surface of the patterned chip. Additional macroscopic connectors can be glued or otherwise attached to the top of the chip to act as additional fluid reservoirs or as interfaces to macroscale pumping systems. Those of skill in the art will be familiar with a variety of methods and mechanisms that are useful for the formation and use of microfluidic devices and such methods and mechanisms (i.e. sample injectors, valves, pumps, mixers, bead-packed microcolumns) may be incorporated herein, as desired or necessitated by the specific design. Exemplary methods and mechanisms are described, for example, in Piyasena et al., 2004 "Near-simultaneous and real-time detection of multiple analytes in affinity microcolumns." *Analytical Chemistry* 76: 6366-273 and Piyasena et al., 2006 "An electrokinetic cell model for analysis and optimization of electroosmotic microfluidic pumps." *Sensors and Actuators B* 113: 461-467, each of which is hereby incorporated by reference.

To prepare the chip for experimentation, it may first be loaded with aqueous buffer solution via capillary action. In the t-shaped geometries, the detection microchannel (i.e. microchannels 40 and 54 in FIGS. 3 and 4, respectively) is typically filled first until the entire array is saturated. At this point, the remainder of the chip can be filled by introducing buffer through the sample stream leg. Once the entire chip is filled, fluid flows in each leg of the system through the fluid manipulation source.

Regardless of the particular geometry used to configure the microchannels, reactions regions and detection regions, as stated above, each reaction region includes a target concentrating mechanism which may, for example, take the form of a plurality of biologically active beads. Formation of packed bead microcolumns may be accomplished by the introduction of biologically-active beads through a bead packing stream. Grates in the sample and waste streams can be constructed as described above in order to sequester the beads in one or more desired locations (e.g. the reaction regions). For example, in the device shown in FIG. 3, it may be desirable to sequester the beads in the junction of lanes 40 and 42. In some embodiments, a physical occlusion in the bead packing stream may not be necessary to maintain the packing because fluid flow can be controlled using the fluid manipulation source. Alternatively, beads may be packed sequentially such that a frit can be formed from reactive beads after the biologically active beads are introduced. See e.g., Piyasena M E et al., 2004 "Near-simultaneous and real-time detection of multiple analytes in affinity microcolumns." *Analytical Chemistry* 76: 6366-273, which is hereby incorporated by reference.

As stated above, the regardless of the geometry used, the presently-described detectors all employ a target concentration mechanism within the reaction region that is configured to reversibly immobilize receptors within the reaction region. All threat agents, regardless of their source, exert their toxicity at the cellular level, which requires interaction with the cell or cellular triggers. The interaction is often mediated by binding of or interaction between the threat agent and a specific receptor, (or binding partner). For example, nerve agents bind to receptors for neurotransmitters, and Shiga and Cholera Toxins bind glycosides on ion channels. Thus, the agents typically must be able to bind specific receptors in order to affect their desired physiological effect. Accordingly, even if a threat agent has been modified (either through natural mutation or in a laboratory), it will typically retain or include a binding region associated with a target receptor. It is this biological mechanism that is exploited by the presently-described system so as to be able to detect both known and unknown threat agents.

There are a number of biological receptors that are known to be strong targets for CBW agents because binding of these targets by a toxin produces known physiological effects. Consequently, molecules suitable for use in the detection system described herein include specific biomolecules targeted by known classes of threat agents. For example, it is well known that nerve agents (e.g. soman, sarin) interact with the soluble enzyme acetylcholine esterase (AChE). For that reason, AchE may be a suitable receptor for the methodologies described herein. In addition, these agents are known to bind to muscarinic receptors, further amplifying the results of an increased amount of acetylcholine on the parasympathetic nervous system. Thus, solubilized muscarinic receptors may similarly be a suitable receptor for use with the methodologies described here.

Another class of nerve agents is reflected in the shellfish paralysis agents (SPAs), also known as paralytic shellfish toxins (PSTs), which block ion channels. Dinoflagellates, (the cause of "red tide") produce toxins which are accumulated in filter feeders such as shellfish. Similar compounds are found in the toxic organs of puffer fish. These toxins are related to the archetypal molecule saxotoxin and its analogues. A naturally occurring compound, saxiphilin has been found in the blood of many marine invertebrates. Saxiphilin is a known receptor for SPAs, the function of which is to sequester SPA-type compounds. Accordingly, the hydrophilic protein receptor saxiphilin may also be suitable for use with the methodologies described here.

Bacterial agents exhibit their pathology through specific toxins. Specific cellular targets for many threats such as anthrax have been identified. See, e.g., Bradley K A, et al., 2003. "Anthrax toxin receptor proteins" *Biochemical Pharmacology* 65: 309-14, which is hereby incorporated by reference. In addition, generalized targets, such as T-cell receptors, which react to a variety of pathogenic bacteria, ranging from relatively benign infections with *Pseudomonas aeruginosa*, to plague and tularemia, have been discovered. See e.g. Gossman et al., 2002. "Quantitative structure-activity relations for γδT cell activation by phosphoantigens." *Journal of Medicinal Chemistry* 45: 4868-74, which is hereby incorporated by reference.

Enterotoxins represent an important general class of bacterial toxins. These food or water born toxins cause severe, hemorrhagic diarrhea often leading to death. They usually consist of two subunits: one that binds to receptors on the intestinal mucosa, and the other which permeates the cell membrane. The non-toxic subunits of these could be used for detection. Since many of these toxins share similar binding sites (e.g. shiga, cholera and enteropathic *E. coli*), known receptors could be used to screen for other toxins of this class.

Viral agents, although not currently weaponized, could, in fact, lead to a new generation of bioterror. Among the possible threats include hantaviruses, filoviruses (e.g. Ebola), and variations of pox viruses. See e.g. Su J R. 2004, "Emerging Viral Infections" *Clinical and Laboratory Medicine* 24: 773-95, hereby incorporated by reference. Viruses require entry into cells for propagation and the first step in cellular infection is binding to a cellular receptor. For hantaviruses, for example, β-3 integrins, present on endothelial cells, seem to be the major target. Ebola and other lentoviruses seem to enter through dendritic receptors. See e.g. Watson, et al., 2002. "Targeted transduction patterns in the mouse brain by lentivirus vectors pseudotyped with VSV, Ebola, Mokola, LCMV, or MuLV envelope proteins." *Molecular Therapy* 5: 528-37, hereby incorporated by reference.

Some of the most potent potential toxins, e.g. aflatoxin, exert their effects on the cell in part by intercalating into DNA. Therefore, detection of these agents might be easily accomplished using double stranded DNA as receptor.

Accordingly, it can be seen that there are a large number of known receptors that are suitable for use with the present disclosure.

As stated above, in some embodiments, the target concentration mechanism takes the form of a biologically active bead. According to one specific embodiment, the desired receptor (or receptors) are encased in a lipid bilayer formed around a silica (or other suitable) bead. As shown in FIG. 5, the biologically active bead includes the silica bead 100, the lipid bilayer 102 and the receptor 104. It is this biologically active bead that is then packed into the reaction region of the detector. A sample suspected of including a toxin analyte 106 is introduced (for example as described above) under suitable conditions to allow for binding, producing a bead having a receptor-ligand complex 108 bound thereto. Surfactant is then introduced to disrupt the lipid bilayer around the bead and release the bound receptor-ligand complex resulting in the naked silica bead 100, unbound receptor 104 (which may or may not be present, depending on the amount of analyte initially present in the sample), excess toxin analyte 106 (which also may or may not be present, depending on the amount of analyte initially present in the sample), and the released receptor-ligand complex 108. The unbound toxin analyte 106 and bound receptor-ligand complex then travels to the detection region.

In general, the unbound toxin analyte, unbound receptor, and bound receptor will have different electrokinetic mobility due to the difference in their molecular weight and charge. Some embodiments may take advantage of this difference by electrokinetically separating the different molecules before detection. Accordingly, movement of the unbound toxin analyte, unbound receptor, and bound receptor may be accomplished by electrophoresis. Alternatively, the detector may employ other (or additional) mechanisms for separately detecting the unbound receptor and the bound receptor. For example, the separation channel (i.e. the channel leading from the reaction region to the detection region) may employ physical or other modifications configured to allow the bound and unbound receptor to be differentiated. For example, physical barriers may be present which slow the progress of the larger bound receptor-ligand complex relative to the smaller unbound receptor. Alternatively or additionally, the separation channel may by modified with a hydrogel such as poly(ethylene glycol) ("PEG"), polyacrylic acid or polyacrylamide, and/or include gel monoliths formed from polyacrylamide or the like, porous polymer monoliths, choromotographic packing, patterned silica nanospheres, etc. Moreover, it will be understood that alternative, non-electrokinetic, separation methods such as pressure driven separation may be employed.

In a still further embodiment, the target concentrating mechanism comprises a stimuli-responsive polymer (SRP) (Also referred to herein as a "smart polymer" or "smart surface"). Stimuli-responsive polymers are described, for example, in U.S. Pat. Nos. 6,491,061, 6,615,855, and 6,755,621, and U.S. patent application Ser. No. 11/682,396, each of which is hereby incorporated by reference. See also, Fu et al., 2003 "Control of molecular transport through stimuli-responsive ordered mesoporous materials." *Advanced Materials* 15:1262-6; Ista et al., 2001 "Synthesis of poly(N-isopropylacrylamide) on initiator-modified self-assembled monolayers. *Langmuir* 17:2552-5; Ista et al., 1999 "Surface-grafted, environmentally responsive polymers for biofilm release." *Appl Environ. Microbiol* 65: 1603-9; Balamurgan et al., 2003 "Thermal response of poly(N-isopropylacrylamide) brushes probed by surface Plasmon resonance." *Langmuir* 19: 2545-9; and Filipcsei, et al., 2007 "Magnetic Field-Responsive Smart Polymer Composites." *Adv Polym Sci* 206: 137-189, each of which is also incorporated by reference. In general, the term "stimuli-responsive polymer" refers to synthetic, naturally occurring and semi-synthetic polymers which exhibit rapid and reversible changes in conformation as a response to environmental stimuli. Examples of environmental stimuli can include temperature, pH, ionic strength, electrical potential, light intensity and light wavelength. As described in these references, the stimuli-responsive polymer can be used to control molecular transport of aqueous solutes. According to one particularly described embodiment, a porous network including SRPs enables dynamic control of size-selective transport. Accordingly, such a porous network could be used in the presently disclosed system as a mechanism to both concentrate and separate bound receptor-ligand complexes from unbound receptors.

As described in the U.S. patent application Ser. No. 11/682, 396, the porous network containing the SRPs make take the form of a bead (which may be referred to herein as a "smart bead.") Those of skill in the art will be familiar with methods for forming beads of mesoporous material. Exemplary methods are described in U.S. patent application Ser. No. 10/640, 249 and U.S. Provisional Patent Application Ser. No. 60/985, 050, each of which is hereby incorporated by reference. See also, Rao et al., 2000 "Encapsulation of poly(N-isopropyl acrylamide) in silica: A stimuli-responsive hybrid material that incorporates molecular nano-valves." *Advanced Materials* 12: 1692-5, which is also incorporated by reference.

Turning now to FIG. 6, a smart bead 110 to which a plurality of receptors 104 have been reversibly absorbed is shown. The smart bead is then exposed to a fluid sample suspected of containing an agent of interest 116. Any agent of interest present in the fluid sample binds the receptors. The smart beads are then exposed to appropriate environmental conditions to allow for release of the receptors from the smart bead. Accordingly, both bound 118 and unbound 116 receptors are released into the fluid flow. In the example shown in FIG. 6, the unbound receptors reach the detection region 126 first and the bound receptor-ligand complexes second.

It is noted that in FIG. 5, both the receptors and the agent of interest are shown bearing detectable labels 109 and 111, respectively and that no labels are shown in the embodiment of FIG. 6. As described elsewhere in the present disclosure, labels may or may not be used, depending on the particular detection system employed. For the proof of concept experiments described in the Example sections below, both the receptors and the agent were labeled, in order to demonstrate that detectable separation of the bound and unbound receptor complexes was achieved. However, it will be understood that labeling of one or more of the various experimental components, while certainly possible, is not necessitated by the methods described herein.

Accordingly, in one embodiment, the biologically active beads of the present disclosure are smart beads decorated with reversibly absorbed receptors, such that the receptors can be released upon exposure of the smart bead to the appropriate environmental stimulus. Methods for decorating smart surfaces with reversibly absorbed receptors are described in Balamurugan et al., 2005 "Reversible Protein Absorption and Bioadhesion on Monolayers Terminated with Mixtures of Oligo (ethylene glycol) and Methyl Groups" *J. Am Chem. Soc.* 127: 14548-14549, which is hereby incorporated by reference. It will be appreciated, of course, that while the smart surface shown in FIG. 6 is in the shape of a spherical bead, any suitable surface shape or configuration may be used including, but not limited to spherical, or non-spherical beads, planar configurations, matrices, etc.

As an exemplary mechanism and method, a microfluidic chip, as described above, may have one or more reaction regions comprising a plurality of smart beads including reversibly absorbed receptors that bind to one or more classes of CBWs. The receptors may be fluorescently or otherwise labeled, or not, as determined by the detection method being used. The sample stream is then passed through the reaction region(s) such that CBW agents, if present, bind to the immobilized receptors. Because the immobilized receptors act to concentrate the threat agent on the beads, extremely sensitive detection is possible, even with arbitrary sample volumes. In the case of the t-shaped configurations, the fluid flow directionality is altered once sampling is completed. Regardless of the configuration used, once sampling is completed, the smart beads are exposed to the appropriate environmental stimulus to effect release of the immobilized receptors. As in the embodiments described above, the bound and unbound receptors then flow through a microfluidic channel, where they are separated, and the timing of the passage of the receptors through the detection region is then determined. As before, the differences in eletrokinetic mobilities between the unbound receptors and bound receptor/agent complexes can be exploited to indicate the presence, concentration, and possibly identity of CBW agents present in the sample.

As stated above, in some embodiments the detection system is based on the differential electrokinetic mobilities of bound and unbound receptors within the microfluidic arrays. Specifically, it is expected that the bound and unbound receptors will separate into two time-separated detectable clusters as they travel through the microfluidic channel towards the detection region. The expected time for unbound receptors ($t_r$) can easily be determined by simply running the experiment without target sample. Accordingly, if a signal is detected at a time point that is statistically different from the expected $t_r$ it can be determined that the sample contains the target agent. Moreover, detecting two time-separated signals may be enough to determine that target is present in the sample.

In another embodiment, the device may include a control lane that operates under the same conditions and responds to the same fluid manipulation source, but which is not exposed to target. Accordingly, by comparing the time point of the signal detected in the control lane with the time point(s) of signal(s) detected in the test lane(s), the user could determine whether or not target is present in the sample. FIGS. 7 and 8 depict two exemplary embodiments of devices including control lanes. In FIG. 7, the device 210 contains two separate lanes, control lane 212 and test lane 214. Control lanes 212 and 214 are both connected to the same fluid manipulation source 216. Accordingly, the user could inject a sample for detection into inlet 218 in lane 214 and an inert fluid, such as electrolytic solution into inlet 220, and encourage movement of the fluid in the microfluidic device using the same fluid manipulation source. In the embodiment depicted in FIG. 8, control lane 222 and test lane 224 are in fluid communication with one another so that identical reaction conditions are achieved in both lanes. However, a fluid manipulation source ensures that fluid does not flow from lane 224 to 222, ensuring the control lane is not contaminated with target from the sample. Those of skill in the art will contemplate that a wide variety of geometries and configurations including control lanes are available and that those provided here are provided only for purposes of illustration.

It will be understood that in some embodiments it may be desirable to determine not only whether or not a CBW threat is present, but to attempt to garner more specific information about the particular threat identified in the sample. Accordingly, the principles of flow cytometry and Affinity Capillary Electrophoresis may be used to develop and build a database of expected ligand/receptor complex behaviors to serve as an aid in analysis of test results. In this embodiment, the target concentrating mechanism, whether in the form of a smart bead or not, may comprise a precisely defined concentration of receptors in order to produce consistent, repeatable results to allow for various analyses of specific previously-identified CBW agents and known potential threats. Flow cytometry, a method of obtaining precise fluorescence spectrometric data from individual particles (e.g. cells or microbeads) is a very useful method for determining the concentration of receptors on the surfaces of beads used to construct affinity microcolumns. See e.g. "Buranda et al., 2002 "Biomolecular recognition on well-characterized beads packed in microfluidic channels." *Analytical Chemistry* 74: 1149-56.

Moreover, flow cytometry can also be used to determine the affinity of receptors toward model CBW-relevant ligands as well as the rate of dissociation of model ligand/receptor complexes. Such information can be used to develop and build the aforementioned database of expected ligand/receptor complex behaviors. For example, it will be understood that agents that bind the same receptor may demonstrate different behaviors during transportation (e.g. based on size, electrochemical composition, or the like) and knowledge of such differences may allow the user to more specifically identify the particular agent present within the sample. As a specific example, such a database may be able to identify the time that a particular agent would be expected to take to travel from the target concentration region to the detection region after release from the target concentration region (i.e. the "travel time" for that agent). Since it would be expected that different threats might have different expected travel times, a user could detect not only the presence of the threat, but also the possible identity of the threat by determining the travel time.

The above-described embodiments have discussed the use of microfluidic channels, which are generally described as channels having at least one dimension in the range of 1-100 microns. However, the present disclosure also provides for the use of nanofluidic channels within the detection device. For the purposes of the present disclosure, nanofluidic channels those channels which are identified as having at least one dimension smaller than one micron. Using fluid volumes in the nanoscale range significantly reduces the size of the sample required.

It should be noted that in nanoscale channels, the electrostatic effects of electro-osmotic flows and steric effects can have profound effects on analyte separations. For example, when a sample including two separate fluorescent dyes—one negatively charged and one positively charged is injected into a nanofluidic device such as that of the present disclosure, electrokinetic separation is faster than and in the opposite direction from a similarly designed microfluidic device, that is, in the nanofluidic device the negatively charged dye travels to the cathode faster than the neutral dye, while in the microfluidic device, the neutral dye travels to the cathode faster than the negatively charged dye. This behavior was demonstrated in a chip using a T-shaped geometry including nanofluidic channels intergrated with microchannels with a hierarchical combination of pattern features ranging over a span of six orders of magnitude—from ~1-cm flow lengths to 50-nm nanofluidic channel widths. See e.g. e O'Biren et al., 2003 "Fabrication of an integrated nanochip using interferometric lithography." *Journal of Vacuum Science and Technology B* 21: 2941-5. Initial demonstrations of molecular flow and separations in these nanochannels offer a unique experimental platform for nanofluidics because for the first time, the Debye screening length is comparable to channel width. This anomalous behavior results from the enhanced importance of screening and fluid/channel-wall interactions in these nanoscale channels. In other words, at the nanoscale, molecular and surface interactions dominate transport. The electrical double layers that arise in solutions of electrolytes due to screening of surface charge at ionic surface are ~10 s of nm wide—comparable to the channel width. The scale of these layers can be controlled by external biasing (analogous to charge transport in field-effect transistors) creating an entirely new approach to fluid control. See e.g. Garcia et al., 2005, "Electrokinetic molecular separation in nanoscale fluidic channels." *Lap Chip* 5, 1271-1276. These behaviors can be studied and catalogued in order to allow for the more precise characterization of CBW threats in sample populations. Moreover, nanofluidic devices such as those described herein can be used as an inexpensive, facile and manufacturable means for creating integrated fluidic circuits that allow the transition from macroscopic fluid handling (e.g. pipettes) to nanoscale dimensions.

Further understanding of the present disclosure may be had by review of the following examples:

EXAMPLE I

Differential Migration of Cholera Toxin Subunit B and $C_5$-Ganglioside $G_{M1}$ Receptor in T-Microchannel Preparation of T-Microchannel T-Microchannel was fabricated with polydimethylsiloxane (PDMS) polymer using soft lithography method. PDMS microchannel was fabricated with three weirs at T cross-section to hold 30 μm beads. The dimensions of microchannel were: NS length 6 cm, WE length 3 cm, WC and EC length 1.5 cm, NC length 1.0 cm, width 300 μm and height 100 μm.

Preparation of Microsphere Supported Lipid Bilayers Incorporated with Receptor Protein 1 mM solution of egg phosphatidylcholine (egg PC) in chloroform (200 μl total volume) was taken in a clear glass tube. 10 μl (2.5 mg/ml) of $C_5$-ganglioside $G_{M1}$ receptor labeled with BODIPY dye was added to egg PC solution. Dry nitrogen gas was bubbled through the solution to dryness, leaving a film at the bottom of the glass tube. The film was subsequently vacuum dried at room temperature for half an hour. After addition of 1 ml of Tris buffer (pH 8.3) the solution was sonicated to optical clarity in a sonication bath. 30 μm glass beads were added to the small unilamellar vesicles dispersions with vortexing for 2 minutes in a microfuge tube. In this manner small unilamellar vesicles spontaneously collapsed into a continuous bilayer incorporated with receptor protein surrounding beads. After sitting for 30 minutes, the beads were then centrifuged and resuspended in buffer, repeating for fifteen times to remove unbound lipid and receptor protein. These glass beads with lipid bilayers and receptor protein were then packed in PDMS T-microchannel with vacuum. FIG. 10 shows a Confocal Microscopy image of 30 μm glass beads with $C_5$-ganglioside $G_{M1}$ receptor labeled with BODIPY dye packed in PDMS microchannel.

Binding, Release and Detection of Toxin Based on Electrokinetic Separation

Cholera Toxin Subunit B was used as a ligand. FIG. 11 shows the voltages applied at different wells for electrokinetic sample injection. Cholera Toxin Subunit B sample was added in E well. Sample was injected due to electrokinetic mobility. Cholera Toxin Subunit B binded to $C_5$-ganglioside $G_{M1}$ receptor on beads and formed the complex. After 20 minutes of sample injection voltages were switched (FIG. 12) and at the same time 10% sodiumdodecylsulfate (SDS) surfactant was added in N well. Due to SDS, receptor-ligand complex and unbound receptor from the beads got released and injected in separation channel (CS). Receptor-toxin complex, unbound receptor and excess toxin eluted in separation channel were detected by Confocal Microscopy at a distance of 7 mm from point 2. FIG. 13 shows the separation order for 4 μM Cholera Toxin. Receptor-toxin complex and receptor were separated and detected due to difference in the electrokinetic mobility. FIG. 14 shows the binding curve for Cholera Toxin Subunit B and $C_5$-ganglioside $G_{M1}$ receptor.

EXAMPLE II

Rapid Prototyping of Microfluidic Chips with Bead-Packed Affinity Microcolumns

A reproducible protocol for rapid fabrication of polydimethylsiloxane (PDMS) microchannels via soft lithography and packing receptor-bearing affinity beads into packed beds of controlled lengths is demonstrated. We have used two microfluidic configurations, straight channels and T-cross section chips. Soft lithography enables the facile redesign and prototyping of channel configurations and dimensions such that chip, microcolumn and analysis parameters can be optimized. Using these techniques, it is possible to generate large numbers of chips for testing of toxin-detection performance under a variety of experimental conditions. We have developed standard operating procedures for microcolumn packing, sample introduction, pumping, analyte capture, analyte release, electrokinetic separation of receptor and receptor/toxin complexes, and finally detection of receptor and receptor/toxin complexes. A number of microfluidic separation matrices have been explored thus far. The results shown below are obtained using traditional microchannel capillary electrophoresis. Our preliminary results suggest that much more efficient separations will be enabled through the integration and use of nanofluidic channel arrays.

Preconcentration of Toxin on Biomimetic Beads and Elution of Receptor-Toxin from Microcolumns.

We have demonstrated preparation of biomimetic affinity beads with GM1 as a receptor incorporated within EggPC lipid bilayers supported on silica beads. Cholera toxin and other enterotoxins bind to the GM1 receptor. The GM1/cholera toxin B pair is one of the best-studied receptor/toxin systems and thus this model receptor/toxin system is well suited for these studies. We have demonstrated the efficient binding of cholera toxin B to GM1 supported on biomimetic beads packed in microfluidic channels. Preconcentration of the toxin was achieved using a microcolumn packed with receptor bearing affinity beads. FIGS. 15A-15C show the fluorescence images of beads packed in PDMS straight channel. In order to demonstrate detectable separation of the unbound toxin, unbound receptor, and bound receptor-toxin complex, both the toxin and the receptor were labeled in this experiment. Accordingly, the signal shown in the upper panels (which would appear red in a color image) is from cholera toxin B conjugated with ALEXA FLUOR 555® fluorophore and the signal shown in the lower panels (which would appear green in a color image) is from BODIPY FL® fluorophore conjugated to GM1 receptor. FIG. 15A shows 30 μm beads before cholera toxin B injection. FIG. 15B shows the packed beads after injection of 100 nM cholera toxin B. Existence of both green and red signals in the micrographs confirms the specific binding of cholera toxin B to the GM1. After preconcentration surfactant elution was used for removal of receptor and receptor-toxin complex and lipid bilayer assemblies from the biomimetic beads for subsequent electrokinetic analysis (FIG. 15C). We have demonstrated that surfactant elution method is an easy and efficient method for achieving receptor and receptor/toxin injection into the separation channel. We have examined the efficacy of several different ionic and nonionic surfactants (e.g., TRITON-X-100® surfactant, TWEEN-20® surfactant, sodium dodecyl sulfate) in elution, separation and detection of GM1 and GM1-cholera toxin complex. Among the surfactants and concentrations studied, we concluded that 10 wt % sodium dodecyl sulfate is best suited for detection of the GM1-cholera toxin system. FIG. 16 shows detection of GM1 and cholera toxin B by elution with 10 wt % sodium dodecyl sulfate after preconcentration of 100 nM cholera toxin B on GM1 bearing affinity beads. The solid line represents the elution of GM1 (Bodipy FL fluorescence) while dashed line (Alexa 555 fluorescence) represents the elution of cholera toxin B. The coincidence of the peaks for the Bodipy FL and Alexa 555 dyes indicates that the eluted GM1 and cholera toxin B are co-migrating in this system. This suggested that monitoring of the GM1 fluorescence alone can be used to detect unlabeled cholera toxin and other toxins (vide infra).

Receptor and Receptor-Toxin Separation by Miceller Microcolumn Electrophoresis.

Figure 17:
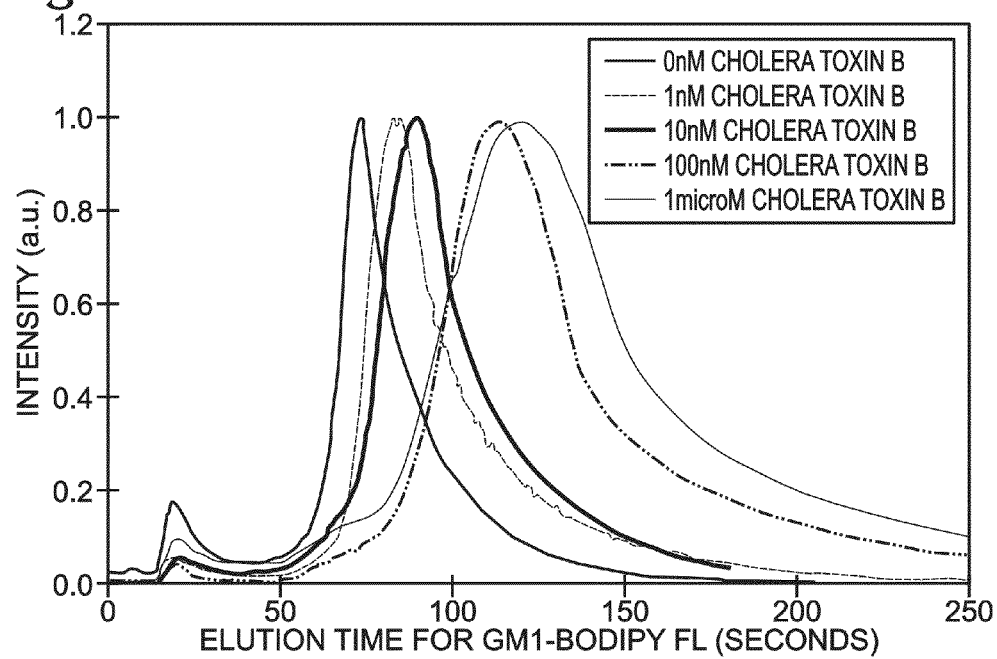
FIG. 17 depicts the elution of GM1 from microcolumns exposed to injections (10 μL) of cholera toxin at various concentrations. 10 wt % sodium dodecyl sulfate was used for elution.
Figure 18:
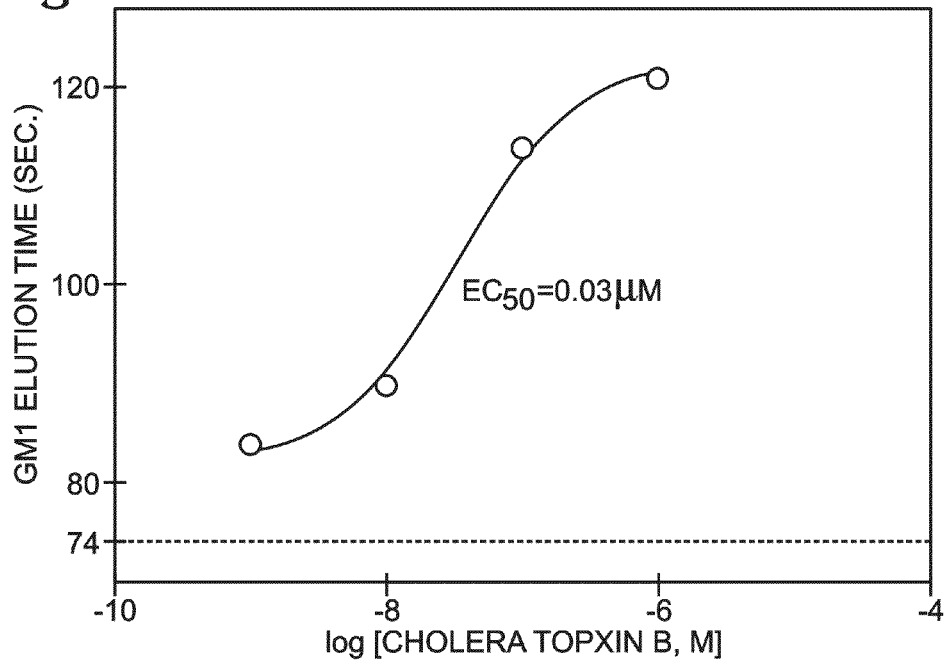
FIG. 18 is a dose-response curve for detection of cholera-toxin by microcolumn capture and capillary electrokinetic elution. Sample volume=10 μL.
Figure 19:
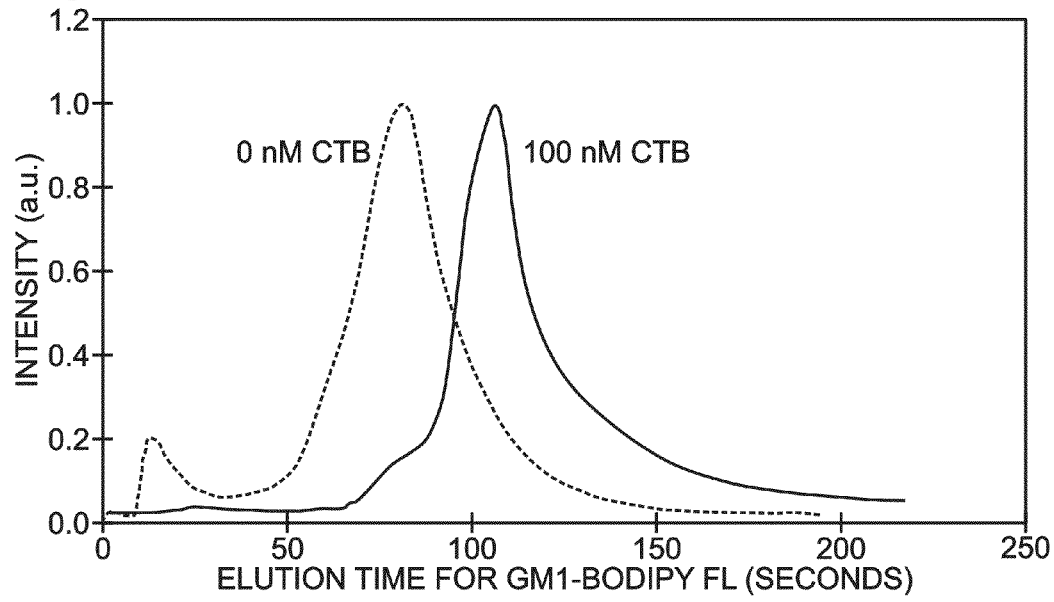
FIG. 19 depicts the elution of GM1 after exposure to duck pond water spiked with 100 nM cholera toxin B. Sample vol.=10 μL.

We studied the elution of GM1-cholera toxin B after injecting 10 μL of aqueous solution of toxin at different concentrations. FIG. 17 shows the electrokinetic elution of GM1 at various cholera toxin B injection concentrations. In each case 10 wt % sodium dodecyl sulfate was used for elution and 200V was applied over 2 cm long channel. The detector was placed 5 mm from start of bead microcolumn. The microchannel was 200 μm wide and 100 μm deep. Tris-glycine buffer (pH 8.4) was used as an elution buffer. The elution time of GM1 for 0 nM cholera toxin B (no toxin present in sample) was 74 seconds. As the concentration of cholera toxin B in the sample increases from 0 to 1 μM, the elution time of GM1 increases from 74 to 121 seconds. FIG. 18 shows the dose-response curve for this system that suggests that this methodology can be used to detect nanomolar concentrations of toxin in 10 μL samples. This corresponds to a detection limit approaching 1 femtomole in this un-optimized system. At 10 wt %, sodium dodecyl sulfate is well above its critical micelle concentration in water. During elution, GM1 and GM1/cholera toxin B complex interact with sodium dodecyl sulfate micelles through hydrophobic interactions. We observed that electrophoresis dominates over electroosmosis for GM1 and GM1-cholera toxin B after their interaction with sodium dodecyl sulfate micelles. As sodium dodecyl sulfate is an anionic surfactant, its micelles are highly negatively charged. GM1 is a 1.5 kDa receptor while cholera toxin B consists of 10.5 kDa subunits. These results suggest that the electrophoretic velocity of micelles incorporating GM1 and cholera toxin is progressively decreased, as more cholera toxin is present. In the absence of cholera toxin, GM1 containing micelles have the highest electrophoretic velocity (and shortest elution time). Importantly, these phenomena result in the capability to quantify cholera toxin concentration by measuring elution times (as opposed to peak areas) and thus to the ability to measure the concentration of unlabeled cholera toxin by measuring the elution time of co-eluted fluorescently labeled GM1.

Detection of Cholera Toxin B in Complex Aqueous Samples.

To demonstrate the superb specificity of this detection strategy, we mixed cholera toxin B into water from a variety of sources including water from the duck pond at the University of New Mexico. 10 μL of 1 μM cholera toxin B was diluted with duck pond water to 100 nM. FIG. 19 shows the electrokinetic elution of GM1 for 100 nM cholera toxin B injection from duck pond water. Results show that specific detection of cholera toxin B is achievable using preconcentration, elution and electrokinetic separation of GM1 and GM1-cholera toxin B in even complex natural aqueous samples.

It should be understood that while much of the description is related to the use of the sensing device and methods described herein for the detection of the presence of CBW threats, the sensing device and methods as described are suitable for use for detection of any suitable ligand. Moreover, as stated, the device may be a useful platform to study nanofluidic interactions.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms “a,” “an,” and “the” include plural reference unless the context clearly dictates otherwise. Thus, for example, a reference to “a host cell” includes a plurality (for example, a culture or population) of such host cells, and so forth. Under no circumstances may the patent be interpreted to be limited to the examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

What is claimed is:

1. A method for detecting the presence of a target in a fluid sample, the method comprising:

introducing a fluid sample to a microfluidic device including a reaction region, a detection region, and a microfluidic channel therebetween;

exposing the fluid sample to a plurality of labeled receptors reversibly immobilized within the reaction region under conditions suitable for the receptors to specifically bind any target present in the fluid sample;

releasing the receptors from the reaction region under conditions such that a substantial portion of the bound target remains bound to the released receptors;

transporting the released receptors through the microfluidic channel such that bound and unbound receptors separate based on differential electrokinetic mobilities; and detecting a signal produced by the arrival of the bound and unbound receptors to the detection region.

2. The method of claim 1 further comprising:

determining an expected detection time for unbound receptors; and comparing the timing of the detected signal to the expected detection time for unbound receptors.

3. The method of claim 2 further comprising determining that the sample contains the target if the detected signal is statistically different from the expected detection time for unbound receptors.

4. The method of claim 1 wherein the receptors contain a fluorescent label and detecting a signal comprises detecting the fluorescent label.

5. The method of claim 1 wherein the receptors are known receptors for chemical biological warfare threat agents.

* * * * *